US006979465B1

(12) United States Patent
Gallardo Ruiz et al.

(10) Patent No.: US 6,979,465 B1
(45) Date of Patent: Dec. 27, 2005

(54) BIOCOMPATIBLE POLYMER SYSTEMS CARRYING TRIFLUSAL OR HTB

(75) Inventors: Alberto Gallardo Ruiz, Madrid (ES); Gema Rodriguez Crespo, Madrid (ES); Julio San Roman del Barrio, Las Matas (ES)

(73) Assignee: J. Uriach & Cia, S.A., Palau-Solita i Plegamans (ES)

( * ) Notice: Subject to any disclaimer, the term of this patent is extended or adjusted under 35 U.S.C. 154(b) by 336 days.

(21) Appl. No.: 10/070,244

(22) PCT Filed: Sep. 1, 2000

(86) PCT No.: PCT/ES00/00335

§ 371 (c)(1),
(2), (4) Date: Jun. 6, 2002

(87) PCT Pub. No.: WO01/17578

PCT Pub. Date: Mar. 15, 2001

(30) Foreign Application Priority Data

Sep. 3, 1999 (ES) ................................. 9902013

(51) Int. Cl.$^7$ .................... A61K 9/14; A61K 47/30; A61F 2/02; C08F 118/02; C08F 220/10
(52) U.S. Cl. .............. 424/486; 424/426; 514/772.3; 526/245; 526/319; 526/323.2; 526/325
(58) Field of Search ................ 424/486, 426; 514/772.3; 526/319, 323.3, 325, 328.5, 245

(56) References Cited

U.S. PATENT DOCUMENTS 4,096,252 A 6/1978 Barra et al.

FOREIGN PATENT DOCUMENTS

| EP | 0 351 314 A2 | 1/1990 |
| EP | 0 596 615 A1 | 5/1994 |
| GB | 2167665 A | 6/1986 |
| WO | WO 97/41164 A1 | 11/1997 |

OTHER PUBLICATIONS

Luo et al, "Synthesis and evaluation of a Amphoteric copolymer HTB as driling fluid derivative" Huaxue Yu Shengwu Gongcheng, 10(5), 55-56 (chinese) 2003, English Abstract.*

G. Rodriguez et al., "New resorbable polymeric systems with antithrombogenic activity," *Journal of Materials Science: Materials in Medicine*, 1999, pp. 873-878, vol. 10, Kluwer Academic Publishers.

* cited by examiner

*Primary Examiner*—Carlos A. Azpuru
(74) *Attorney, Agent, or Firm*—Rothwell, Figg, Ernst & Manbeck

(57) ABSTRACT

New biocompatible polymeric systems carrying triflusal or HTB are described which result from the polymerization of a monomer A of the acrylic or vinylic type and carrying triflusal or HTB, wherein triflusal or HTB are linked to the remainder of the molecule of said monomer through an in vivo hydrolysable covalent bond, and optionally a second polymerisable monomer B. These new polymeric systems are useful as coating for synthetic biomaterials.

26 Claims, 14 Drawing Sheets

(THEMA)

↓ pBO2
  60°C poly[THEMA]

BIOCOMPATIBLE POLYMER SYSTEMS CARRYING TRIFLUSAL OR HTB

The present invention relates to a new series of biocompatible polymeric systems, and more specifically to a new series of biocompatible polymeric systems carrying triflusal or HTB. The invention also relates to a process for their preparation, as well as to their uses, particularly as coatings for prostheses and other devices that are in contact with blood during use.

BACKGROUND OF THE INVENTION

The use of synthetic materials in the field of cardiovascular surgery and particularly in the reconstruction of the vascular system has been one of the greatest advances in this field. The materials used must not only possess suitable physicochemical properties such as flexibility, hydrolytic stability and fatigue strength, but it is essential that they exhibit a good blood biocompatibility or hemocompatibility. The contact of the prosthetic devices with the blood flow leads to the deposition of plasmatic proteins on the surface of the material and to the activation of the coagulation cascade, generating a thrombogenic surface.

No material has yet been found that can be regarded in a strict sense as non-thrombogenic, although certain materials have been used with success in the manufacture of big-diameter (>6 mm) vascular prostheses. Thus, for example, during the last decades commercially available synthetic vascular grafts based mainly on meshes woven or knitted with polyester (Dacron®), polyamide (Nylon®) or polytetrafluoroethylene (PTFE, Teflon®) fibres as well as porous, expanded PTFE (Goretex®) systems have been used. Whereas this type of prostheses works relatively well when used to substitute big-diameter vessels, the failure rate at short- or mid-term is quite high when they are used to substitute small- or medium-calibre vessels due to the appearance of thrombosis. It is therefore still necessary to improve the materials used up to now for this kind of applications.

Triflusal, whose chemical name is 2-acetyloxy-4-trifluoromethylbenzoic acid, is a platelet aggregation inhibitor marketed for the treatment of thromboembolic disorders. Its main metabolite, known by the acronym HTB and whose chemical name is 2-hydroxy-4-trifluoromethylbenzoic acid, also exhibits a remarkable platelet aggregation-inhibitory activity. Both compounds are disclosed in the patent U.S. Pat. No. 4,096,252.

The present invention provides a new series of biocompatible polymeric derivatives carrying triflusal or HTB, which, when used as coatings for the surface of prostheses and other devices that are in contact with blood during use, improve the thrombogenic properties of said devices.

DESCRIPTION OF THE INVENTION

The present invention relates to a polymeric compound of relative general formula I

(I)

wherein:

A represents a residue of a polymerisable acrylic or vinylic monomer carrying triflusal or HTB, wherein triflusal or HTB are linked to the remainder of the monomer molecule through an in vivo hydrolysable covalent bond;

B represents a residue of a second polymerisable monomer;

m and n represent the molar fractions of the monomers A and B in the polymer so that m+n is always 1 and m is always different from 0;

and wherein the A and B units are distributed randomly in the polymer.

The present invention also relates to a process for the preparation of a polymeric compound of formula I which comprises the radical polymerization of a monomer A and optionally a second monomer B in the molar fractions m and n, respectively, in the presence of a polymerization initiator, in a suitable solvent.

As mentioned above, the polymeric compounds of the present invention are useful as coatings for the surface of synthetic materials or materials of non-biological origin (to which we will jointly refer throughout the present specification as non-biological materials) which in use are in contact with blood. Due to the fact that the polymers of the present invention carry triflusal or HTB, compounds with a remarkable antiaggregating activity, which are gradually released through the hydrolysis of the covalent bond that links them to the rest of the polymeric system, the application of the polymers of the present invention on the surface of said non-biological materials improves the thrombogenic properties thereof. The polymeric compounds of the present invention can be used in principle to coat any device or article having a surface that is going to be in contact with the blood during use, and specially to coat vascular prostheses, particularly those of small or medium calibre, as well as artificial cardiac valves and stents or vascular springs used in arteriosclerotic processes.

The present invention therefore also relates to the use of a polymeric compound of formula I as coating for non-biological materials, and particularly as coating for vascular prostheses, artificial cardiac valves and stents.

The invention further relates to the use of triflusal or HTB for the preparation of biocompatible polymeric compounds for coating non-biological materials, particularly vascular prostheses, artificial cardiac valves and stents.

The present invention further relates to a device or article which comprises a surface of a non-biological material that is going to be in contact with blood during use coated with a polymer carrying triflusal or HTB of formula I, and particularly to vascular prostheses, artificial cardiac valves and stents coated with a polymer carrying triflusal or HTB of formula I.

The present invention further relates to a process for preparing said devices or articles which comprises coating the desired device or article with a polymer carrying triflusal or HTB of formula I.

In the polymeric compounds of the present invention triflusal or HTB are linked to the rest of the polymeric system through hydrolysable covalent bonds. As mentioned above, triflusal or HTB are gradually released through the hydrolysis of said covalent bonds. Due to this, the polymeric compounds of the present invention can also be used as controlled delivery systems for triflusal or HTB and may therefore be useful for the treatment or prevention of all those diseases for which triflusal or HTB are indicated. The present invention therefore also relates to the use of a polymeric compound of formula I as a controlled delivery system for triflusal or HTB, having utility in therapy. Moreover, the present invention also relates to the use of a polymeric compound of formula I for the manufacture of a medicament for the treatment or prevention of the disorders for which triflusal or HTB are indicated and more particularly for the treatment or prevention of thromboembolic disorders. The present invention further relates to a pharmaceutical composition which comprises a polymeric compound of formula I and one or more pharmaceutically acceptable excipients. Said compositions can be prepared following conventional procedures, well known to those skilled in the art.

Throughout the present specification and particularly in formula I, the term residue of a polymerisable monomer, whether acrylic, vinylic or of a different type, shall be understood as the residue resulting from the polymerization of the corresponding monomer. Thus, for example, when the polymerisable monomer corresponding to B is N,N-dimethylacrylamide, in formula I B represents in fact the residue of said monomer once polymerized, as shown below:

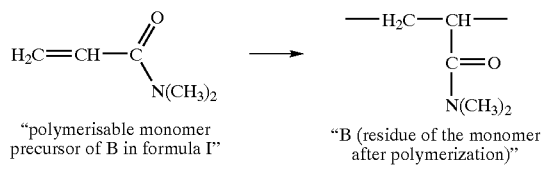

"polymerisable monomer precursor of B in formula I"

"B (residue of the monomer after polymerization)"

Unless otherwise specified, the nomenclature A and B will be used throughout the present specification to refer without distinction to the polymerisable monomer or to the corresponding polymerized residue in the polymer of formula I.

In formula I, A represents a residue of any polymerisable acrylic or vinylic monomer carrying triflusal or HTB. The expression "carrying trifusal or HTB" means that the monomer comprises a molecule of triflusal or HTB linked to the rest of the acrylic or vinylic moiety through a covalent bond that is hydrolysable in vivo, that is under physiological conditions. A preferred group of monomers carrying triflusal or HTB for the preparation of the polymers of formula I are those corresponding to formula II:

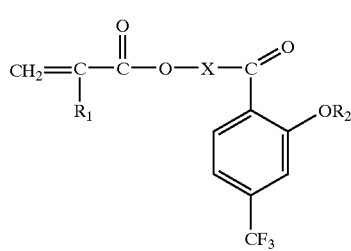

(II)

wherein:
R$_1$ represents hydrogen or C$_{1-4}$ alkyl;
R$_2$ represents —COCH$_3$ or hydrogen;
X represents —(CH$_2$CH$_2$O)$_p$—; and
p represents an integer from 1 to 100.

Within the compounds of formula II, those compounds wherein R$_1$ represents methyl and p represents 1 are particularly preferred.

These monomers carrying triflusal or HTB, useful for the preparation of the polymers of formula I, are novel and form a further aspect of the present invention.

With regard to B, this represents a residue of a second polymerisable monomer, so that when B is present in a polymeric compound of formula I (that is, when n is different from 0) the resulting compound is a copolymer, whereas when B is absent (that is, when n is 0) the resulting compound is a homopolymer. Examples of possible meanings for B include, among others, 2-hydroxyethyl methacrylate, methyl methacrylate, methyl acrylate, N-vinylpyrrolidone, acrylic acid, methacrylic acid, acrylamide, N,N-dimethylacrylamide, vinyl acetate and 2-acrylamido-2-methylpropanesulfonic acid. Furthermore, monomer B can also be another polymerisable monomer carrying triflusal or HTB.

Although the present invention encompasses all the compounds mentioned above, a preferred group of compounds of the present invention are those polymeric compounds of formula I wherein the hydrolysable covalent bond through which triflusal or HTB are linked is a carboxylic ester bond.

Another preferred group of compounds are those compounds of formula I wherein n represents 0.

Another preferred group of compounds are those compounds of formula I wherein n is different from 0.

A more preferred group of compounds of formula I are those polymeric compounds corresponding to relative formula Ia:

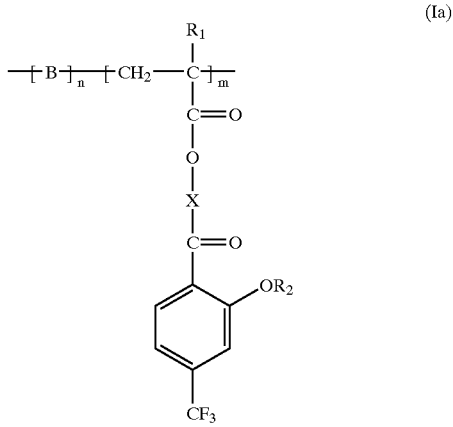

(Ia)

wherein:
R$_1$ represents hydrogen or C$_{1-4}$ alkyl;
R$_2$ represents —COCH$_3$ or hydrogen;
X represents —(CH$_2$CH$_2$O)$_p$—;
p represents an integer from 1 to 100; and
B, m and n have the previously described meaning.

A still more preferred group of compounds of the present invention are those compounds of formula Ia wherein R$_1$ represents methyl and p represents 1.

A particularly preferred group of compounds are those compounds of formula Ia wherein R$_1$ represents methyl; p represents 1 and n represents 0.

Another particularly preferred group of compounds are those compounds of formula Ia wherein R$_1$ represents methyl; p represents 1 and n is different from 0. Within this group of compounds, those compounds wherein B represents a residue of 2-hydroxyethyl methacrylate, methyl methacrylate, methyl acrylate, N-vinylpyrrolidone, acrylic acid, methacrylic acid, acrylamide, N,N-dimethylacrylamide, vinyl acetate and 2-acrylamido-2-methylpropanesulfonic acid are preferred, and those compounds wherein B represents a residue of N,N-dimethylacrylamide or 2-acrylamido-2-methylpropanesulfonic acid are still more preferred.

The molecular weight of the polymeric compounds of the present invention can vary within a broad range, being preferred for use as coatings for non-biological materials those polymeric compounds of formula I with an average molecular weight between 10000 and 100000 Daltons.

The polymeric compounds of formula I can be prepared by any of the known methods of radical polymerization. For example, they can be prepared by polymerization in a solution of the desired monomer or monomers in a suitable solvent in the presence of a polymerization initiator. Said polymerization must be carried out in the absence of oxygen.

As initiator any compound described in the literature for such purpose can be used, for example benzoyl peroxide, lauroyl peroxide, cumene peroxide, butyl perbenzoate, 2,2'-azobisisobutyronitrile (AIBN) or 2,2'-azobisisopentanoic acid, among which benzoyl peroxide and 2,2'-azobisisobutyronitrile are preferred. The amount of initiator to be used will depend upon the molecular weight that it is desired to obtain, and will be easily determined by those skilled in the art.

The solvent used to carry out the polymerization can vary depending on the nature of the monomers used; anybody skilled in the art will be able to easily determine the most appropriate solvent for each case. Anyway, as examples of suitable solvents we can mention dioxane, dimethylformamide, isopropanol, dioxane/water mixtures, chloroform, dimethylsulfoxide, acetone, acetone/dioxane mixtures and acetone/water mixtures, among which the use of polar solvents such as dimethylformamide or solvating solvents such as dioxane or dioxane/water mixtures rich in dioxane are preferred.

The reaction temperature will depend on the initiator used and will also be a determining factor in the molecular weight of the resulting polymeric system, as will be known by those skilled in the art, in general, a temperature between 50 and 70° C. will be appropriate.

The time of polymerization required is not too long, due to the nature of the radical polymerization reactions and the fact that they are addition chain reactions; in general we have found that polymerization times between 6 to 24 hours are sufficient to reach high monomer to polymeric system conversions, although in some cases longer polymerization times might be necessary.

The polymers of formula I are finally isolated using conventional methods, for example by precipitation in a suitable solvent such as ethanol, methanol, isopropanol, hexane, heptane or diethyl ether. In general, it is advisable to use a high precipitant/solution ratio, that is of at least 10 times the volume of precipitant with regard to the volume of solution, to guarantee a good precipitation.

The acrylic or vinylic monomers carrying triflusal or HTB can be prepared in general through the formation of the covalent bond between a suitable acrylic or vinylic derivative and triflusal or HTB, or a reactive derivative thereof, following similar procedures to those described in the literature for the preparation of said type of covalent bonds.

Processes for preparing triflusal or HTB are described in the US patent mentioned above (U.S. Pat. No. 4,096,252).

As stated above, the polymeric compounds of the present invention can be used as coatings for non-biological materials such as prostheses, stents and the like, improving the thrombogenic properties of said materials. Said coatings can be prepared in general by immersion of the surface to be coated in a diluted solution, for example 1–2% w/v, of the desired polymer in a suitable solvent such as dimethylformamide, ethanol, water/ethanol mixtures or dioxane/ethanol mixtures.

The following examples are included herein to illustrate the preparation and uses of the compounds of the present invention. In any case they are to be understood as limiting the scope of the invention in any way.

In the following examples, polymers were analyzed by $^1$H and/or $^{13}$C nuclear magnetic resonance (NMR) spectroscopy in the particular conditions mentioned in each case.

The molar fractions m and n in the copolymers were determined by $^1$H-NMR analysis. Due to the experimental error of the technique, the values of said molar fractions may vary by up to a 5%.

The average molecular weights were determined by Gel Permeation Chromatography (GPC) using a Perkin Elmer apparatus equipped with an isocratic pump LC 250 and a refractive index detector series 200. Data were adquired with a PL-DCU (Polymer Laboratories). Samples were eluted using a set of 3 polystyrene—divinylbenzene pL-gel columns of 500, 104 and $10^5$ Å of nominal pore size (Polymer Laboratories).

EXAMPLE 1

Preparation of 2-(methacryloyloxy)ethyl 2-acetyloxy-4(trifluoromethyl)benzoate (THEMA)

Figure 1:
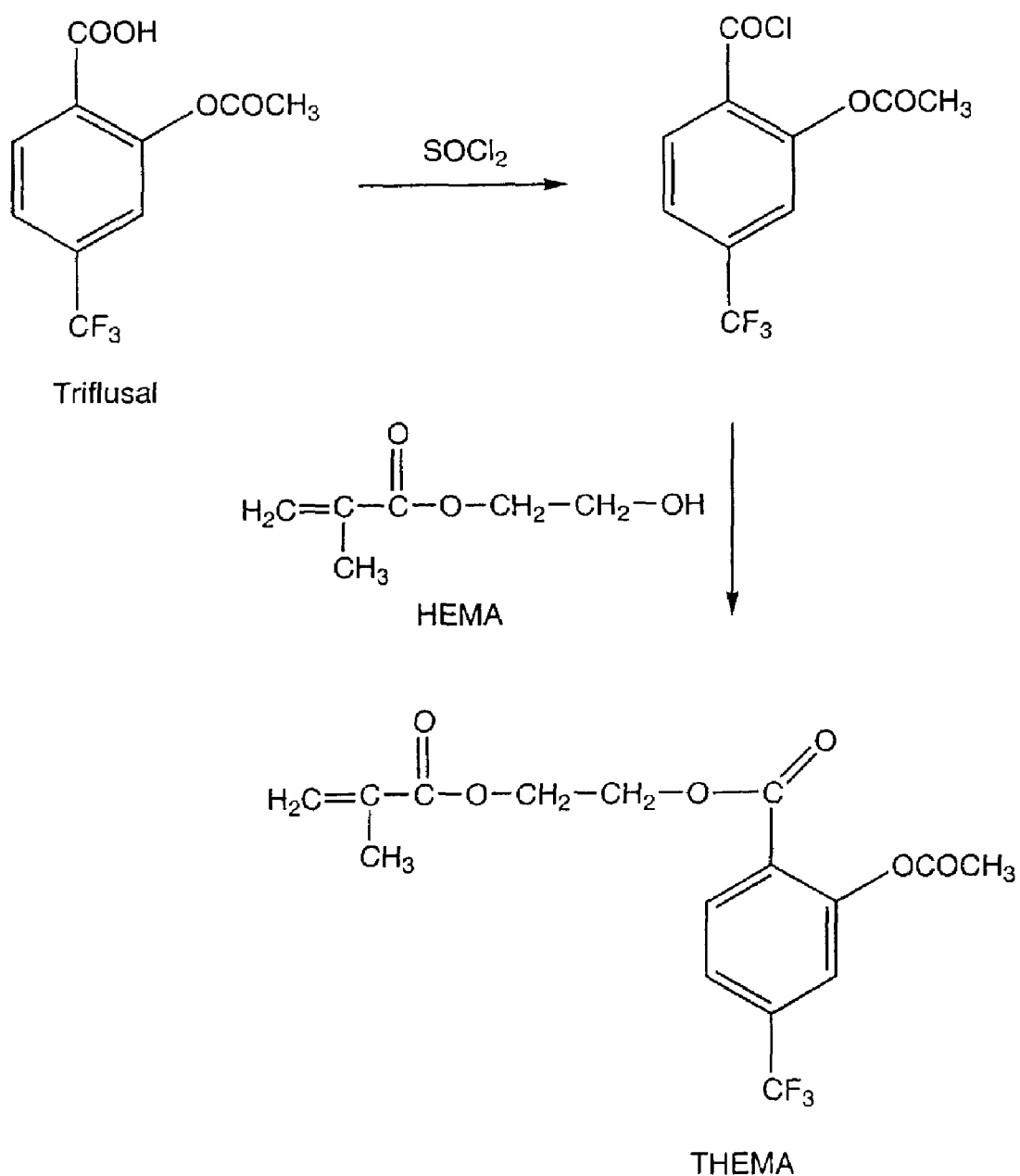
FIG. 1 shows the synthesis of the monomer carrying triflusal described in example 1.

The preparation of this compound is shown in the scheme of FIG. 1.

a) 2-Acetyloxy-4-(trifluoromethyl)benzoic acid chloride

In a round-bottomed flask 0.1 mols of triflusal were reacted with 70 mL of $SOCl_2$, the flask was connected to a refrigerant and the reaction was heated at reflux for 4 h, under magnetic stirring. Next, the unreacted $SOCl_2$ excess was removed by distillation, first at atmospheric pressure and then at reduced pressure. Then, the desired acid chloride was isolated by distillation at reduced pressure. The yield of the reaction was 64%.

$^1$H-NMR (DMSO-d$_6$, 300 MHz, 20° C.); δ: 8.1 (d, 1H, arom), 7.7 (d, 1H, arom), 7.6 (s, 1H, arom), 2.3 (s, 3H, CH$_3$COO—).

b) 2-(Methacryloyloxy)ethyl 2-acetyloxy-4-(trifluoromethyl)benzoate (THEMA)

In a flask were mixed 0.025 mols of 2-hydroxyethyl methacrylate (HEMA) and 5.21 mL Et$_3$N (0.025 mols) in 100 mL of diethylether as solvent. To this mixture, 0.025 mols of the acid chloride obtained in step a) dissolved in diethyl ether was added dropwise, under nitrogen flux and at room temperature. Once the acid chloride addition was complete, the reaction was kept under stirring for 24 hours. The precipitated triethylamine hydrochloride was removed by filtration. The filtrate was washed first with water containing some drops of concentrated HCl, and then with water several times. The aqueous phase was discarded and the organic phase was dried over anhydrous MgSO$_4$. Finally, ether was removed under vacuum until constant weight. The yield of the reaction was 52%.

$^1$H-NMR (DMSO-d$_6$, 300 MHz, 20° C.); δ: 8.1 (d, 1H, arom), 7.8 (d, 1H, arom), 7.7 (s, 1H, arom), 6.1 and 5.7 (d, m, CH$_2$=C<), 4.6 and 4.4 (t,t, —CH$_2$—CH$_2$—), 2.3 (s, 3H, CH$_3$COO—), 1.9 (s, 3H, CH$_3$—C=).

EXAMPLE 2

Preparation of poly[2-(methacryloyloxy)ethyl 2-acetyloxy-4-(trifluoromethyl)benzoate](poly[THEMA])

Figure 2:
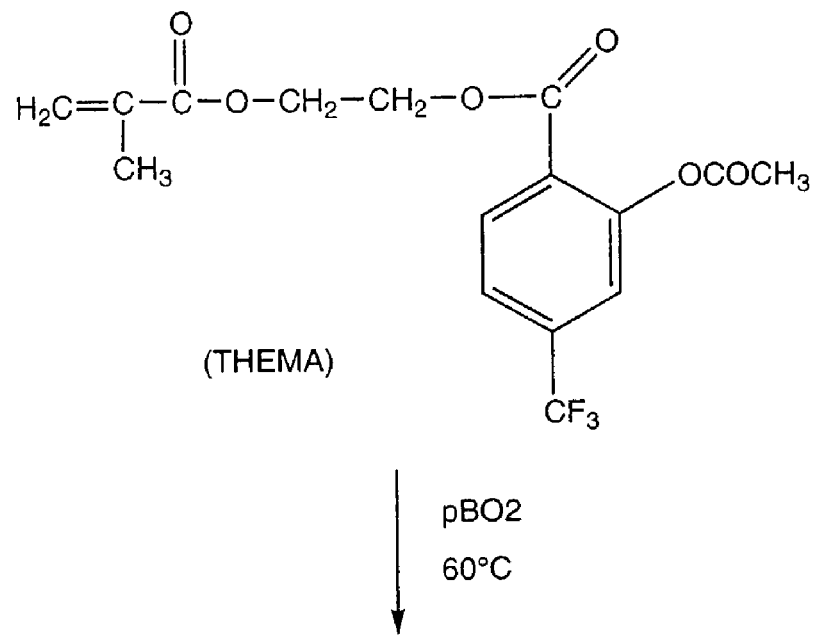
FIG. 2 shows the synthesis of the polymer described in example 2.
Figure 2:
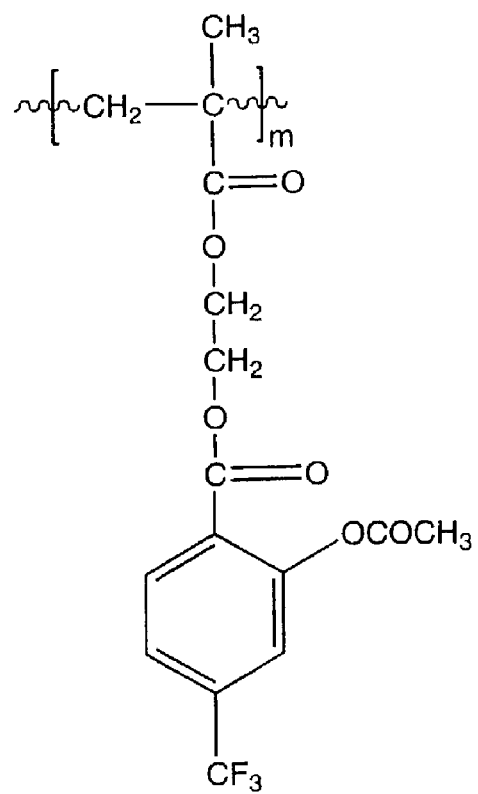

This compound was prepared by polymerization of the monomer carrying triflusal obtained in example I (THEMA). The chemical structure of this compound and its synthesis are shown in the scheme of FIG. 2.

In Pyrex glass ampoules, 5 g of THEMA (obtained in example 1) was dissolved in 28 mL of a (4:1) purified dioxane/acetone mixture, the concentration of the solution thus being 0.5M. Next, benzoyl peroxide (1.5×10$^{-2}$ M) was added as the initiator; for the solution described above 100.8 mg were used. Oxygen was then removed from the solution by bubbling nitrogen (30 min) twice.

The sealed ampoules were immersed in a thermostatic bath at 60° C. for 24 h. After polymerization, the polymer was precipitated by pouring it into an excess of ethanol; to precipitate 5 g of polymer 500 mL of ethanol was used, to which the polymer solution was added dropwise. This operation was carried out in an ice bath. The solution was kept under stirring for 4 h and was then filtered under vacuum. The precipitate thus obtained was washed several times with ethanol, was filtered again, and was then dried in a high vacuum drying oven until constant weight. The yield of the reaction was 90%.

The average molecular weight of this polymer, determined by Gel Permeation Chromatography (GPC), was 48000 Daltons, with a polydispersity index M$_w$/M$_n$ of 1.8.

Figure 3A:
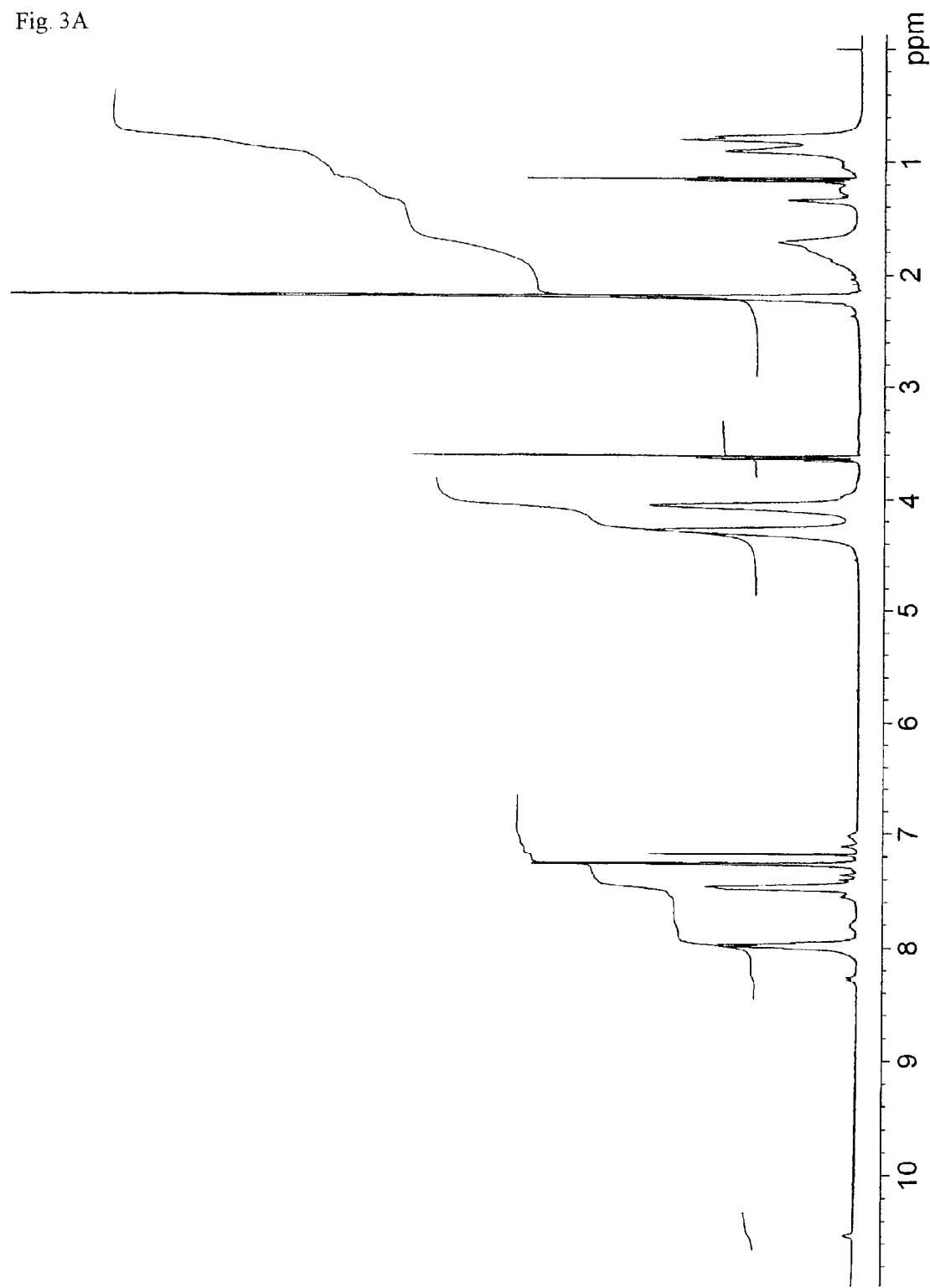
FIG. 3 shows the $^1$H (3A) and $^{13}$C (3B) NMR spectra of the polymer of example 2.
Figure 3B:
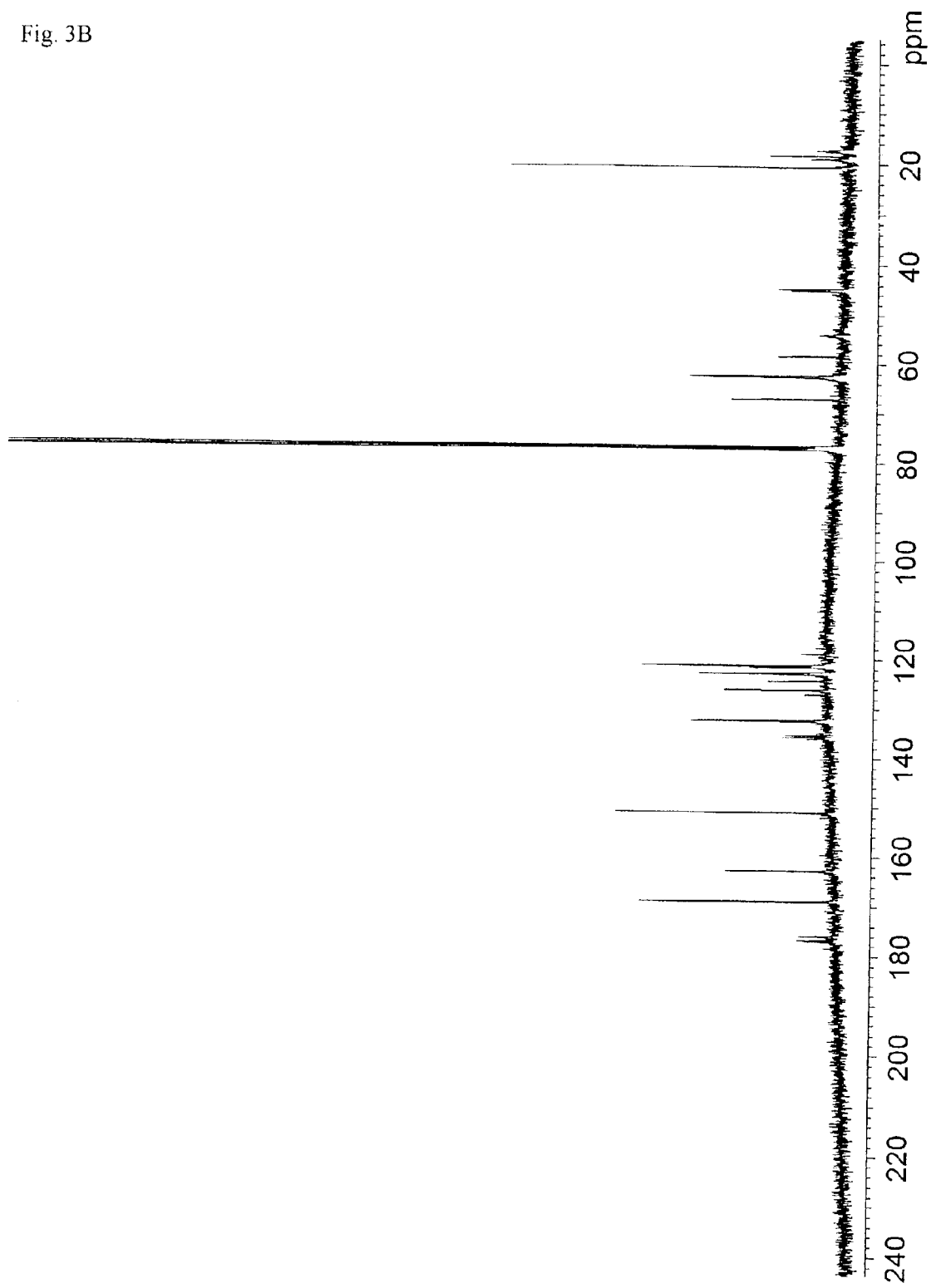

The $^1$H (400 MHz, CDCl$_3$, 45° C.) and $^{13}$C (100 MHz, DMSO-d$_6$, 45° C.) NMR spectra of the polymeric compound obtained in this example are shown in FIG. 3 (A and B).

EXAMPLE 3

Preparation of Copolymers from THEMA and N,N-dimethylacrylamide (DMA) having Various m/n Molar Fractions (poly[THEMA-co-DMA])

Figure 4:
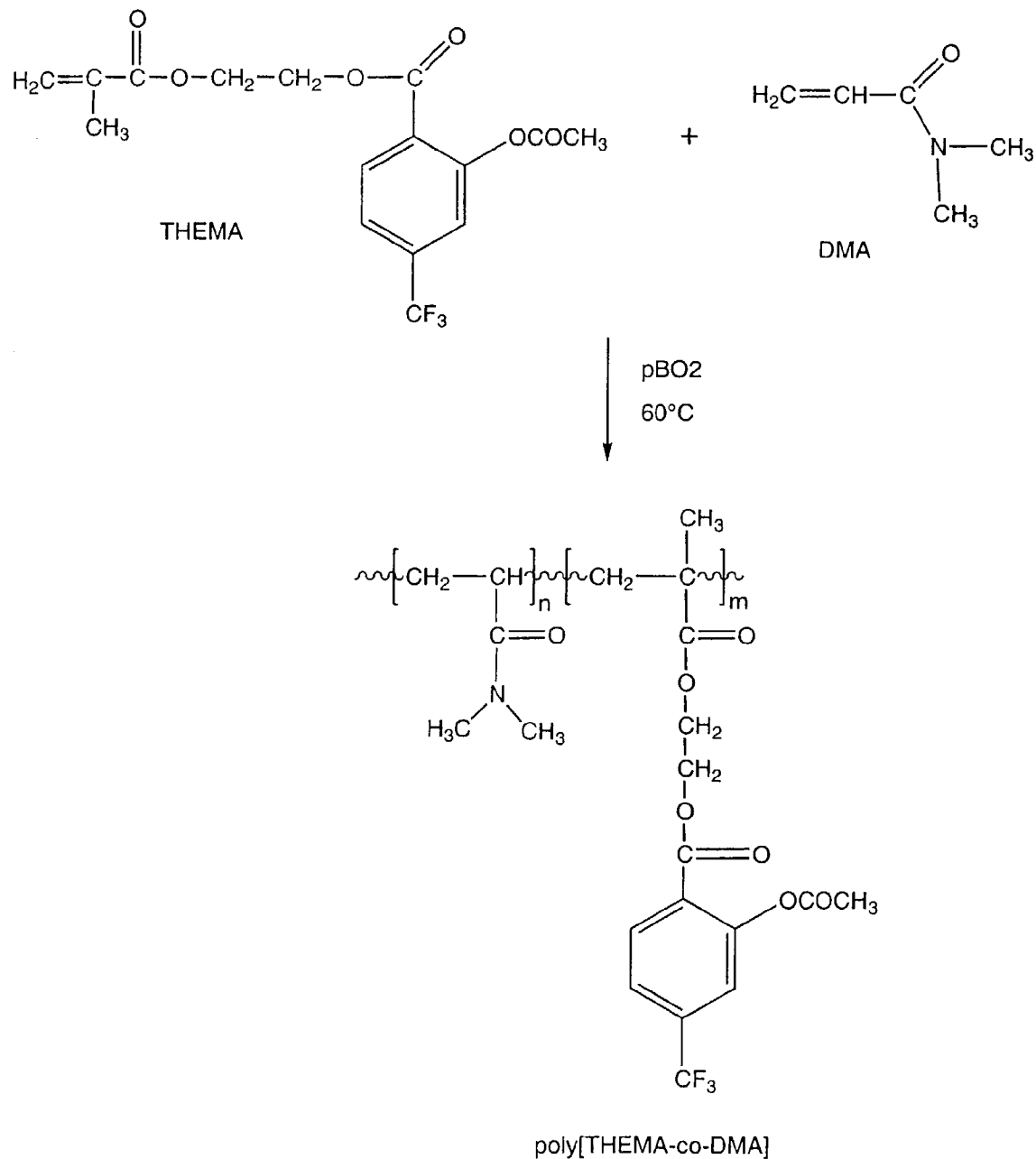
FIG. 4 shows the synthesis of a poly[THEMA-co-DMA] copolymer described in example 3.

The chemical structure of these copolymers and their synthesis are shown in the scheme of FIG. 4.

The preparation of a representative THEMA-DMA copolymer is carried out as follows:

1 g of THEMA (obtained in example 1) and 1 g of DMA was dissolved in 25.75 mL of purified dioxane, the final concentration of the solution being 0.5 M. Next, 46.75 mg of benzoyl peroxide at a concentration of 1.5×10$^{-2}$ M was added and oxygen was removed from the solution by bubbling nitrogen twice for 30 minutes.

The sealed ampoule was immersed in a thermostatic bath at 60° C. for 24 h. The polymer was then precipitated by pouring the resulting solution dropwise into 1 L of diethyl ether. The solution was kept under stirring for 4 h, diethyl ether was then removed by decantation and the precipitate was dried under vacuum until constant weight. The yield of the reaction was 80%.

$^1$H-NMR analysis showed that this copolymer (designated from now on polymer 3A) contains a 52 wt % of THEMA with a m/n molar fraction of 0.18/0.82. GPC determination showed that the average molecular weight was 33000 Daltons, with a polydispersity index of 2.4.

Figure 5A:
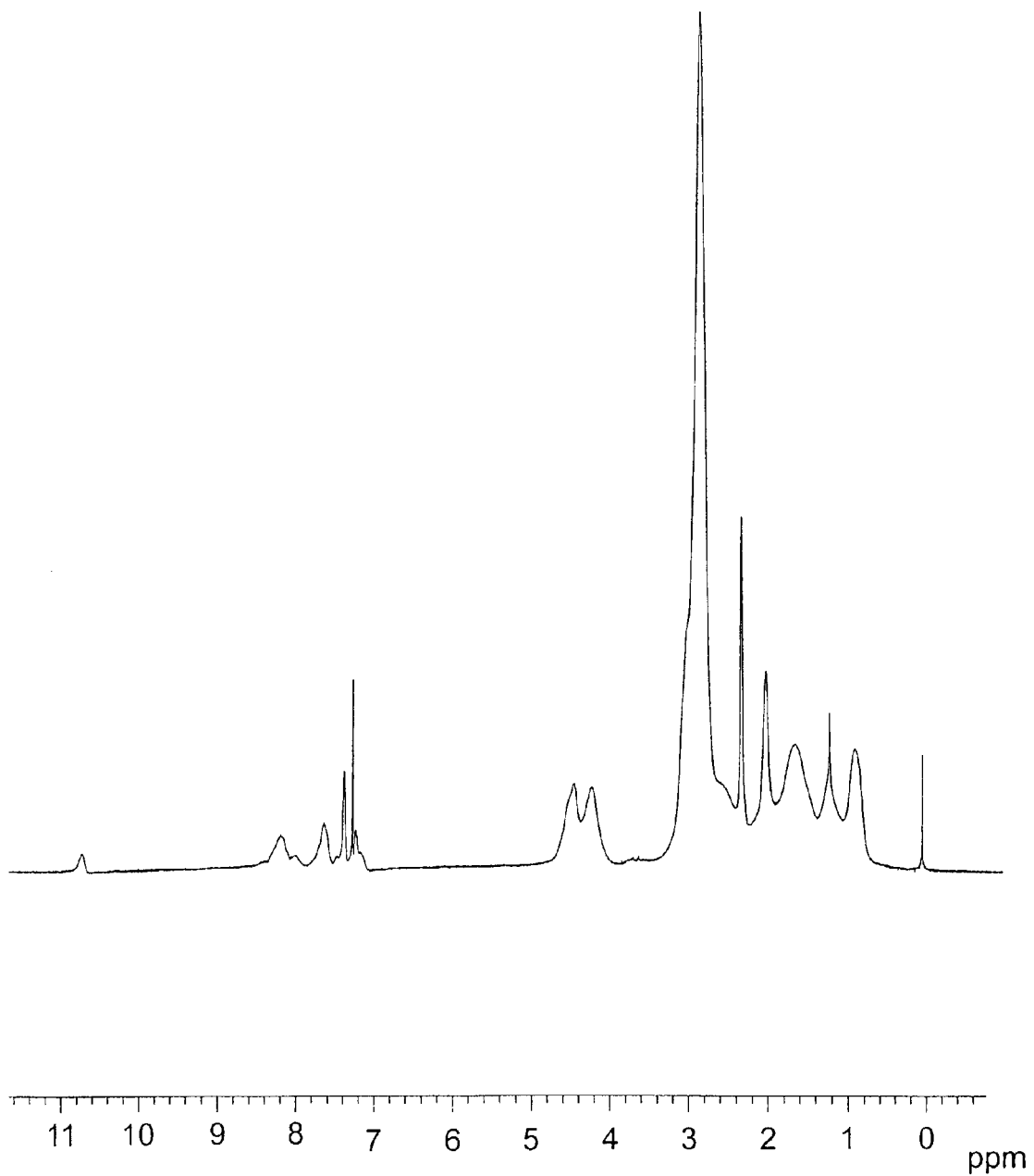
FIG. 5 shows the $^1$H (5A) and $^{13}$C (5B) NMR spectra of the polymer 3A described in example 3.
Figure 5B:
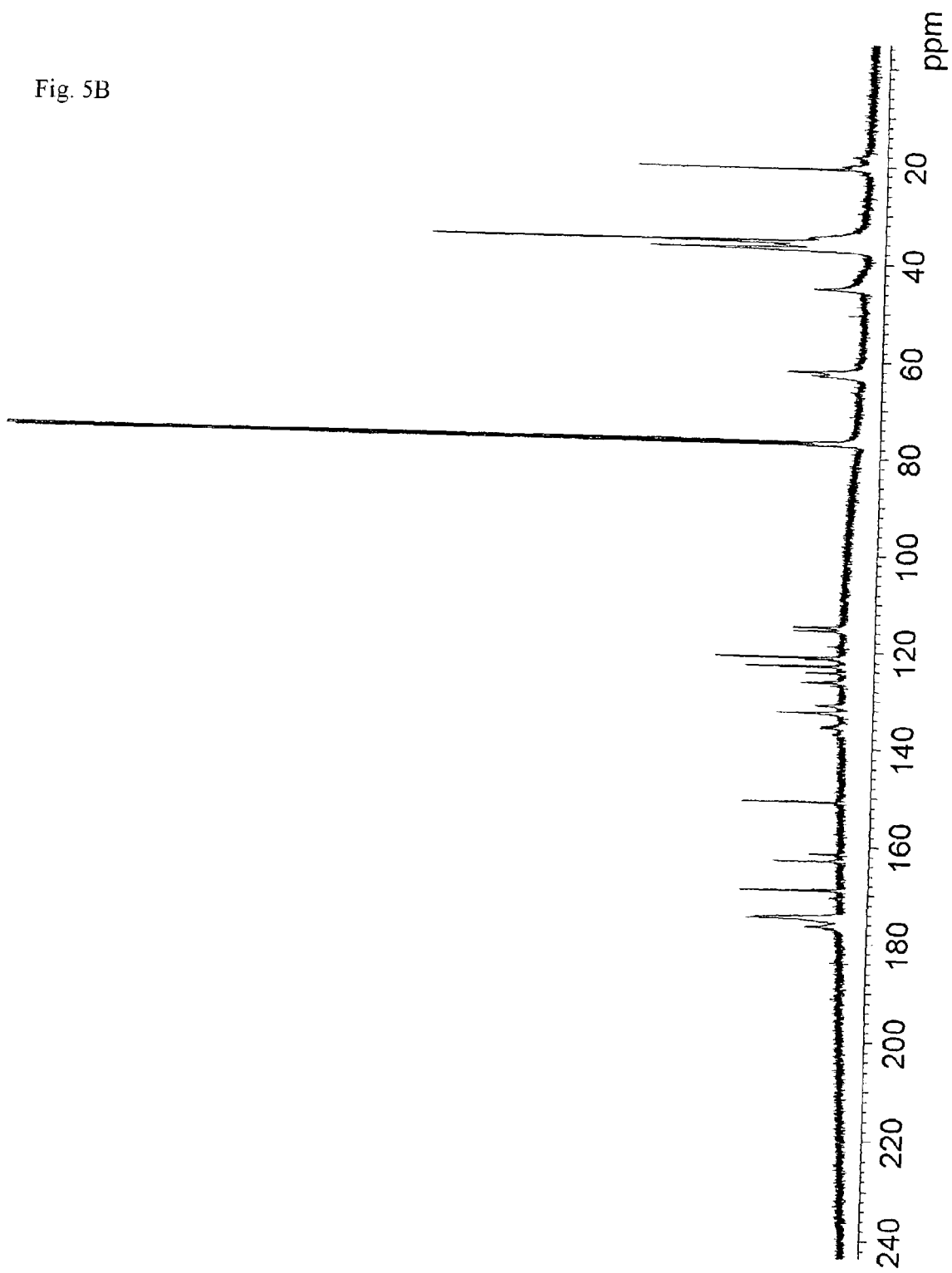

$^1$H (200 MHz, CDCl$_3$, 40° C.) and $^{13}$C (100 MHz, CDCl$_3$, 45° C.) NMR spectra of polymer 3A are shown in FIG. 5 (A and B).

Preparation of other copolymers from THEMA and N,N-dimethylacrylamide (DMA) (poly[THEMA-co-DMA]): Following an analogous procedure to that described to prepare polymer 3A, but changing the proportions of the two monomers (THEMA and DMA) as mentioned below, the following copolymers were obtained:

1) Poly[THEMA-co-DMA] with a molar fraction of 0.20 of DMA in the monomer feed (polymer 3B):

0.13 g of DMA and 1.87 g of THEMA was dissolved in 13 mL of purified dioxane (0.5M). Then, 47.2 mg of benzoyl peroxide at a concentration of 1.5×10$^{-2}$ M was added. The experimental conditions for the polymerization and isolation are the same as mentioned above for polymer 3A.

Yield of the polymerization (percentage conversion in weight): 85%.

Molar fraction m/n=0.79/0.21

Molecular weight M$_n$=38000 Dalton

Polydispersity index M$_w$/M$_n$=2.8

Figure 6:
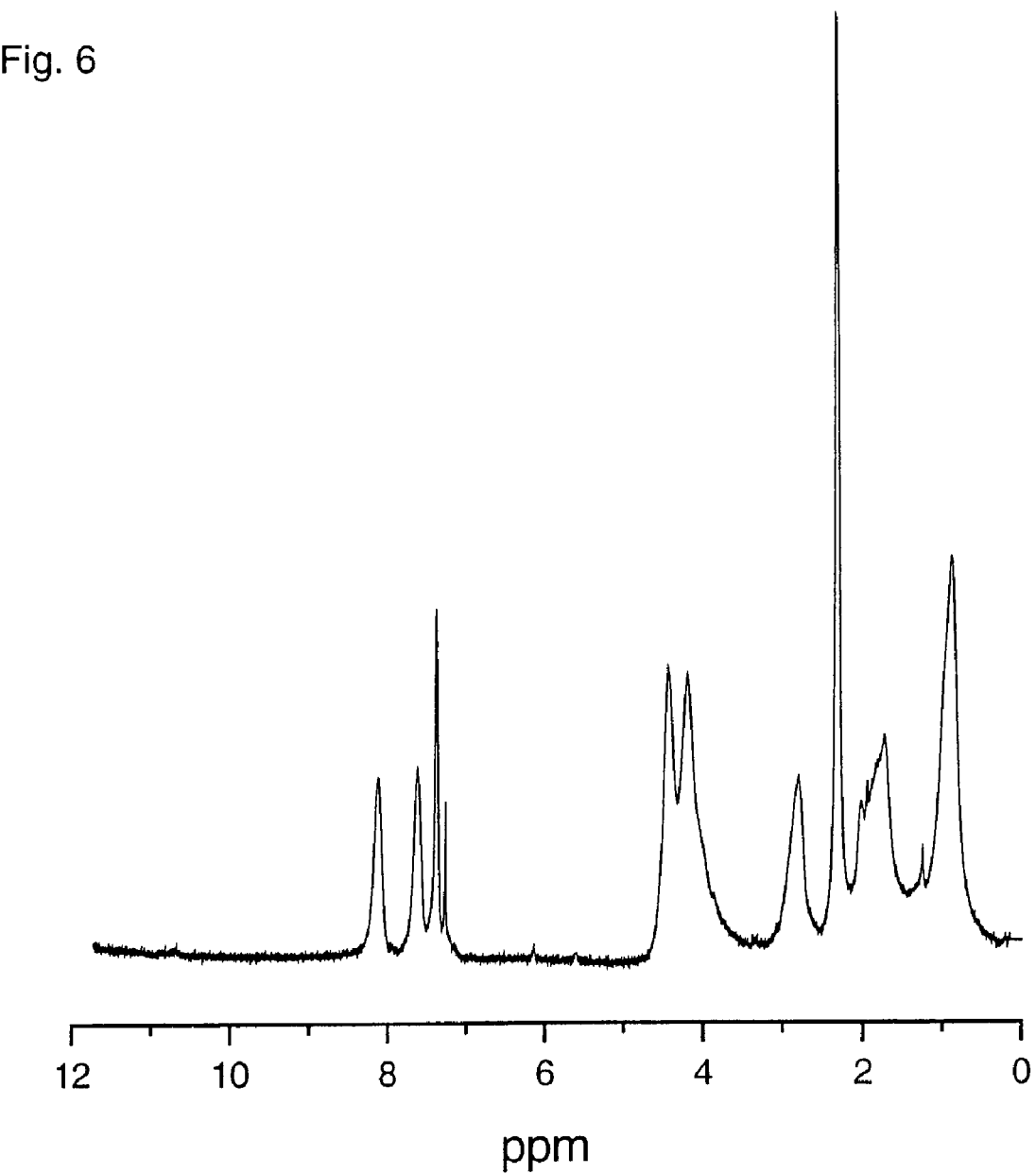
FIG. 6 shows the $^1$H-NMR spectrum of the polymer 3B described in example 3.

$^1$H-NMR spectrum (200 MHz, CDCl$_3$, 40° C.): shown in FIG. 6.

2) Poly[THEMA-co-DMA] with a molar fraction of 0.40 of DMA in the monomer feed (polymer 3C):

0.31 g of DMA and 1.69 g of THEMA was dissolved in 15.65 mL of purified dioxane (0.5M). Then, 56.81 mg of benzoyl peroxide at a concentration of 1.5×10$^{-2}$ M was added. The experimental conditions for the polymerization and isolation are the same as mentioned above for polymer 3A.

Yield of the polymerization (percentage conversion in weight): 91.5%

Molar fraction m/n=0.61/0.39

Molecular weight M$_n$=35000 Dalton

Polydispersity index M$_w$/M$_n$=2.5

Figure 7:
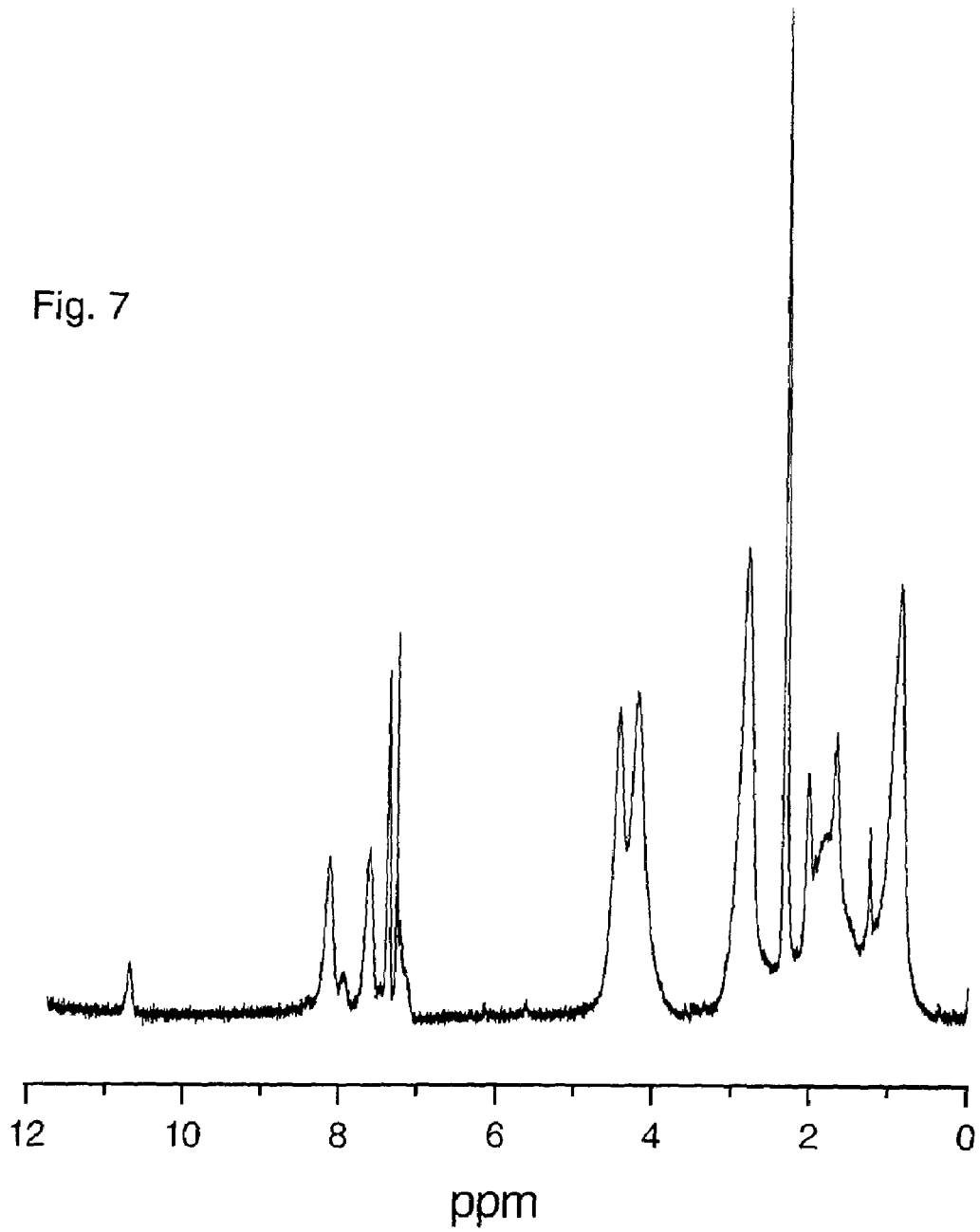
FIG. 7 shows the $^1$H-NMR spectrum of the polymer 3C described in example 3.

¹H-NMR spectrum (200 MHz, CDCl₃, 40° C.): shown in FIG. 7.

3) Poly[THEMA-co-DMA] with a molar fraction of 0.60 of DMA in the monomer feed (polymer 3D):

0.58 g of DMA and 1.42 g of THEMA was dissolved in 19.7 mL of purified dioxane (0.5M). Then, 95.98 mg of benzoyl peroxide at a concentration of $1.5 \times 10^{-2}$ M was added. The experimental conditions for the polymerization and isolation are the same as mentioned above for polymer 3A.

Yield of the polymerization (percentage conversion in weight): 89%

Figure 8:
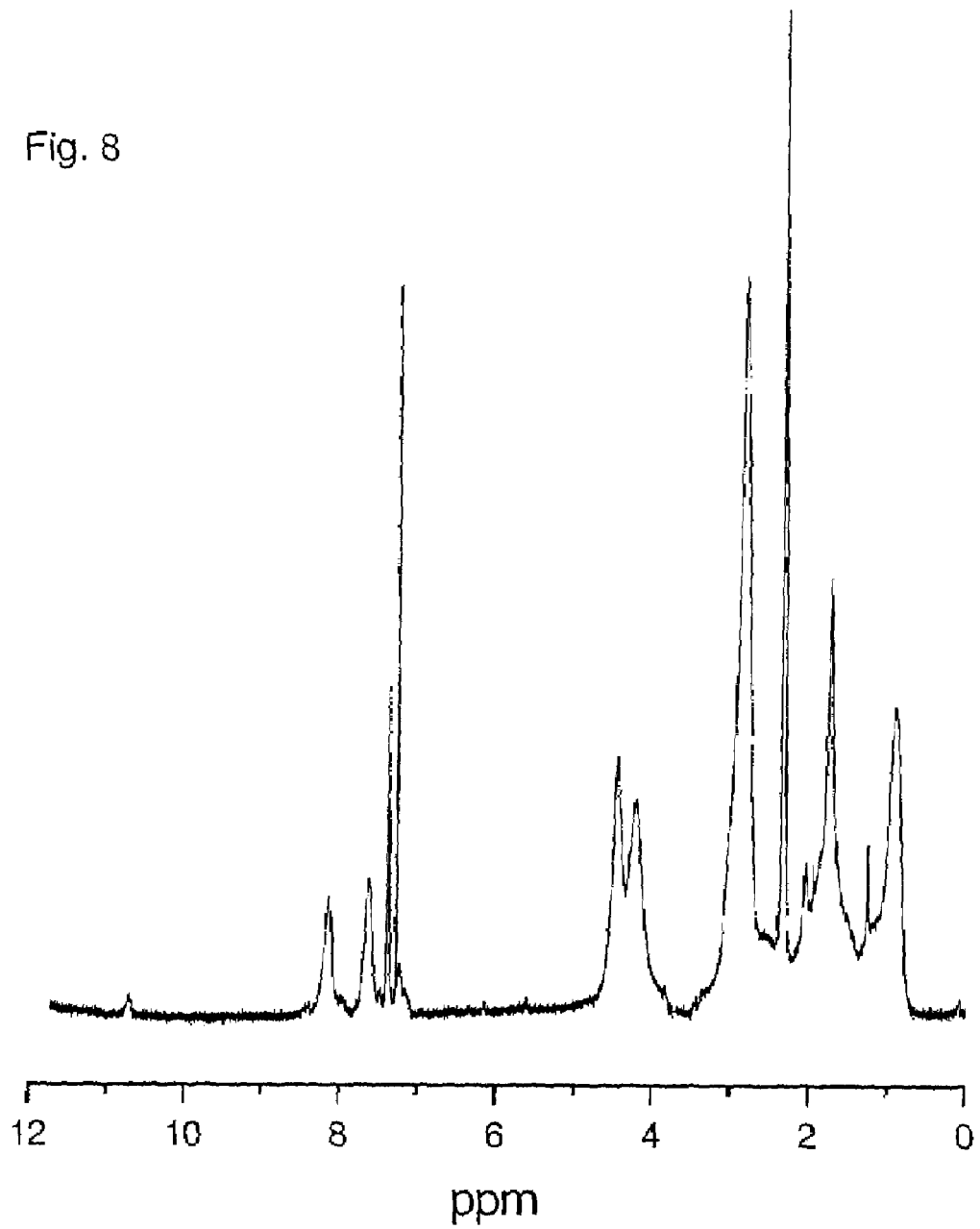
FIG. 8 shows the $^1$H-NMR spectrum of the polymer 3D described in example 3.

Molar fraction m/n=0.42/0.58
Molecular weight $M_n$=34000 Dalton
Polydispersity index $M_w/M_n$=2.6
¹H-NMR spectrum (200 MHz, CDCl₃, 40° C.): shown in FIG. 8.

EXAMPLE 4

Preparation of a Copolymer from THEMA and 2-acrylamido-2-methylpropanesulfonic acid (AMPS) (poly[THEMA-co-AMPS])

Figure 9:
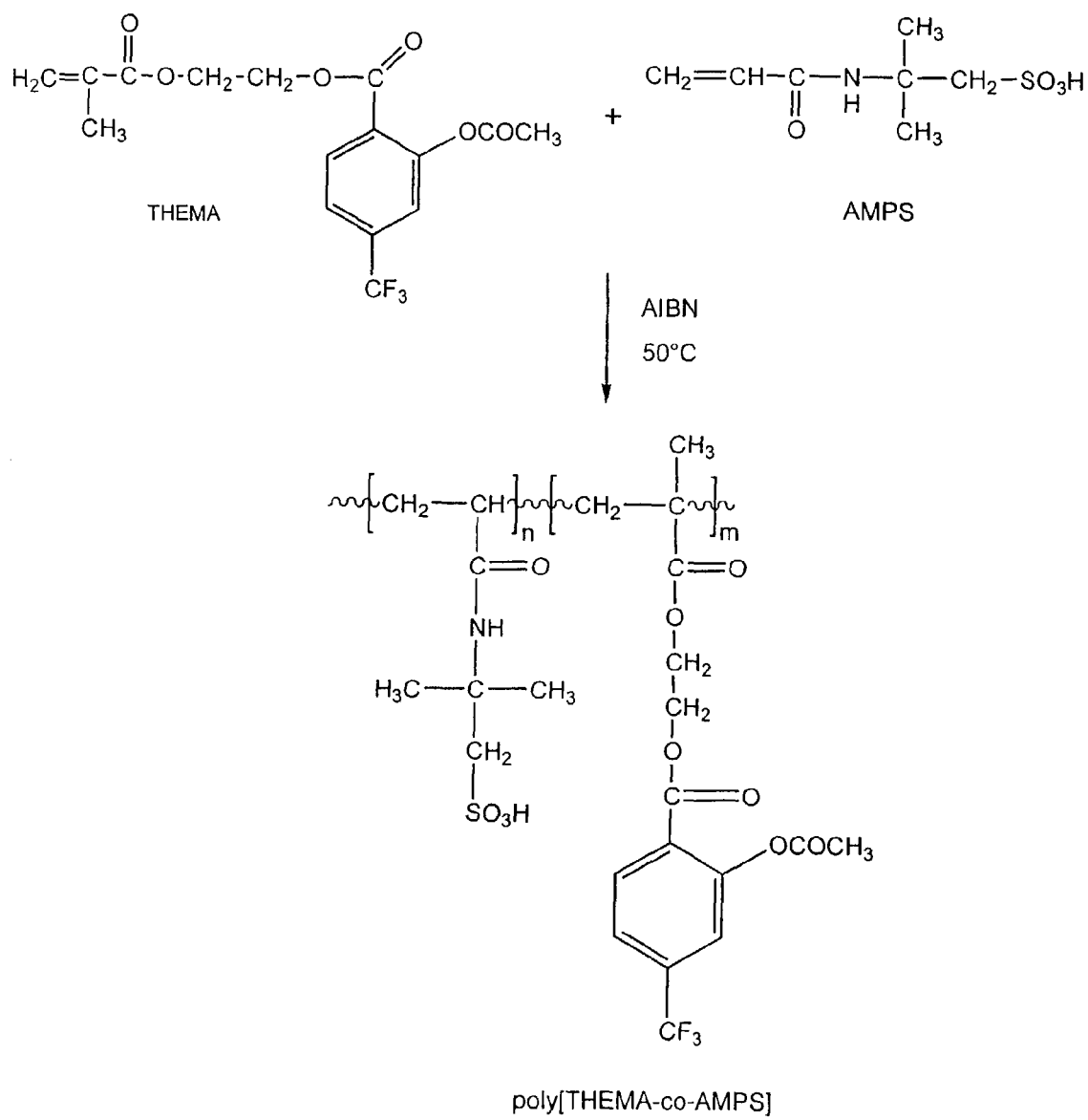
FIG. 9 shows the synthesis of a poly[THEMA-co-AMPS] copolymer described in example 4.

The chemical structure of this polymer and its preparation are shown in the scheme of FIG. 9.

To prepare this polymer, 1 g of THEMA (obtained in example 1) and 0.144 g of AMPS was dissolved in 12 mL of (9:1) purified dioxane/water in a Pyrex glass ampoule, the concentration of the solution being 0.25 M. As polymerization initiator, 2,2-azobisisobutyronitrile (AIBN) at a concentration of $1.5 \times 10^{-2}$ M was used, in this case we used 59.1 mg. Next, N₂ was bubbled through the solution to remove oxygen from the system, twice for 30 minutes.

The sealed flask was immersed in a thermostatic bath at 50° C. for 24 h. The solvent was then partly removed using a rotary evaporator and the polymer was then precipitated with 100 mL of diethyl ether. The solution was kept under stirring for 1 h and the solvent was then removed using a rotary evaporator. The residue was dissolved in 10 mL of distilled water and was then freeze-dried. The yield of the process was 100%.

To purify the polymer, 500 mg of the copolymer obtained was dissolved in 10 mL of chloroform and the copolymer was precipitated by pouring this solution over 100 mL of diethyl ether dropwise, under stirring for 4 h. The polymer was then isolated by filtration under vacuum and was dried until constant weight.

¹H-NMR analysis showed that the copolymer has a m/n molar fraction of 0.77 in THEMA and 0.23 in AMPS.

The average molecular weight of this polymer, determined by GPC, was 43000 Dalton, with a polydispersity index of 2.5.

Figure 10A:
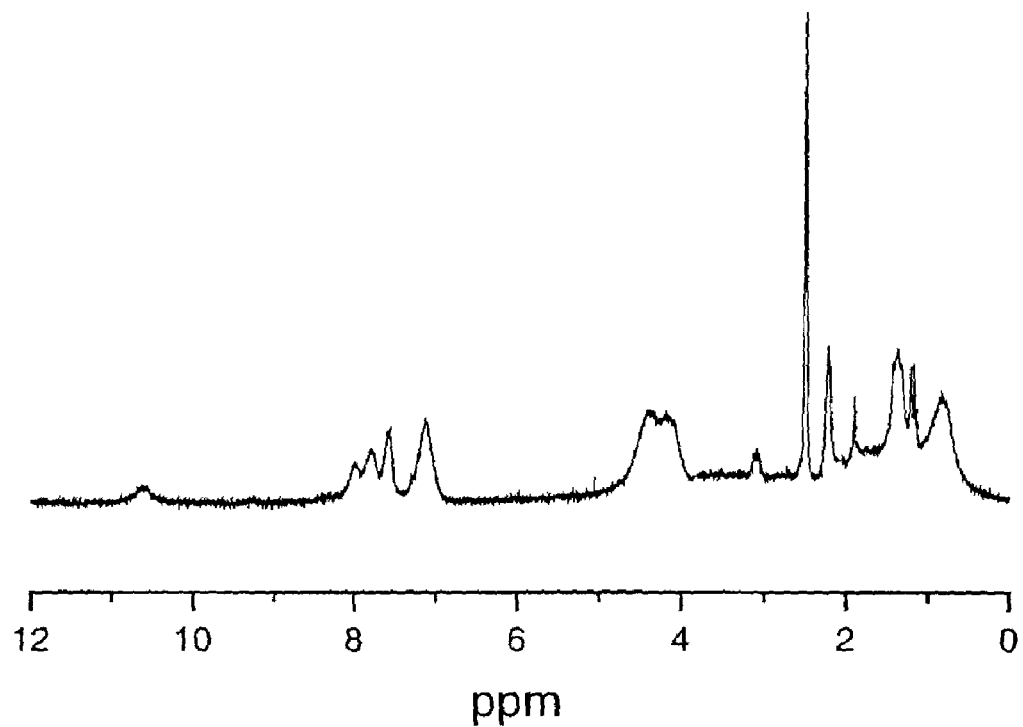
FIG. 10 shows the $^1$H (10A) and $^{13}$C (10B) NMR spectra of the polymer described in example 4.
Figure 10B:
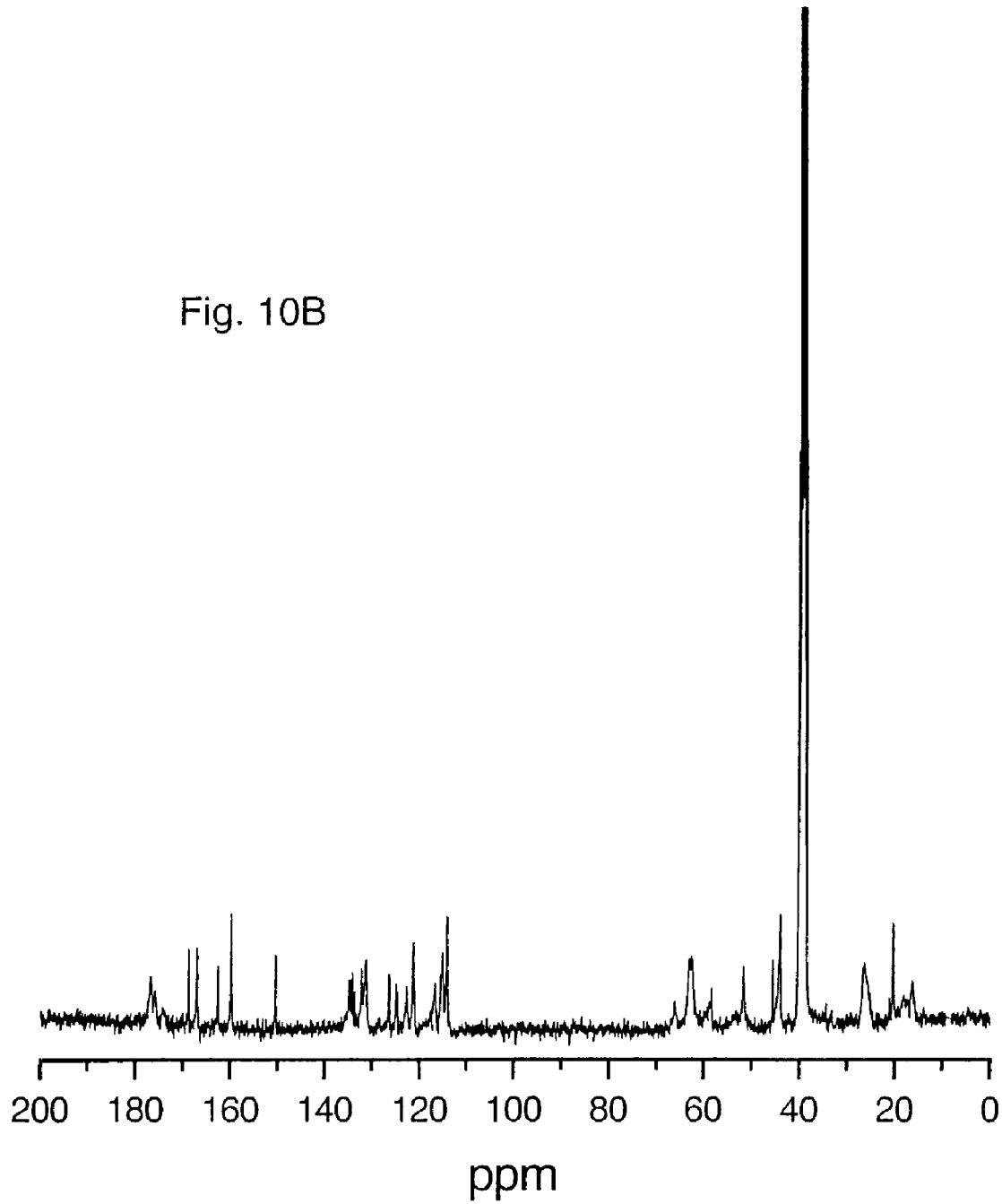

¹H (200 MHz, DMSO-d₆, 40° C.) and ¹³C (300 MHz, DMSO-d₆, 40° C.) NMR spectra of the copolymer described in this example are shown in FIG. 10 (A and B).

EXAMPLE 5

Study of the Release of the Antiaggregating Compound Contained in a Polymer of Formula I in Rat Plasma The release of the antiaggregating agent from the polymers of the present invention can be assessed using an in vitro assay comprising the incubation at 37° C. and under constant stirring of rat plasma to which a solution of the desired polymer has been added and then determine at different times the release of the drug by HPLC. In parallel, and in order to check the linearity and accuracy of the method, the same assay was performed using stock solutions of the drug.

a) Plasma Preparation

Rat plasma was obtained by cardiac puncture. Animals were placed in a chamber previously saturated with diethyl ether; when animals were anesthetized, they were placed in ventral position and were fastened to a table in order to carry out a cardiac puncture through the intercostal space. Blood was transferred to polypropylene tubes containing 20% of 3.2% sodium citrate as anticoagulant, tubes were closed and homogenized manually. Plasma was obtained by blood centrifugation at 2000 g.

b) Solution Preparation

For this assay, the polymer 3A obtained in example 3 was used. This polymer carries triflusal. In this case, due to the well-known hydrolysis of triflusal in aqueous media to give its metabolite, HTB, the release of HTB was followed by HPLC.

The powdered polymer was dissolved in methanol and solutions having a concentration of 0.96 mg/mL, equivalent to a total HTB concentration of 1.4 mM, were prepared. In parallel, the same assay was performed using HTB stock solutions in order to obtain a suitable calibration curve. The concentrations of HTB used were: 1.25 mM, 1.5 mM, 6.2 mM and 9.3 mM.

c) Release Assay

The rat plasma prepared as described in step a) was divided into 0.2 mL volumes which were distributed in polypropylene tubes. To each tube, 10 μL of the polymer solution was added. Tubes were immersed in a bath at 37° C. under constant stirring. Aliquotes were collected at different times and were analyzed by HPLC, using the following conditions:

Waters μBoundapak C-18 column of 3.9×300 mm;
Perkin Elmer LC-250 pump;
UV/V is detector Perkin-Elmer LC-95; λ=305 nm.
Waters 770 Data Module integrator
Mobile phase: aqueous solution of Pic A-methanol, 60:40, microfiltered and degassed.

Before HPLC analysis, samples were prepared by precipitating plasmatic proteins with methanol 1:5, followed by centrifugation at 15000 rpm for 10 min. The supernatant was mixed with an identical volume of mobile phase, microfiltered and injected into the chromatograph.

d) Results

Figure 11:
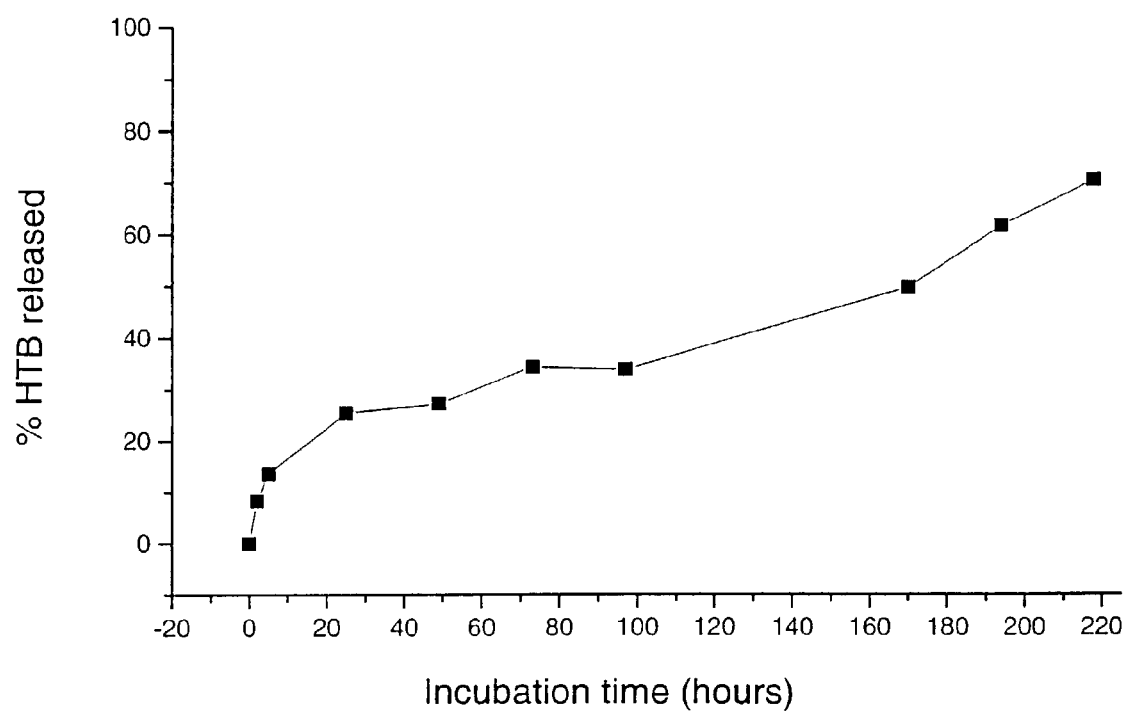
FIG. 11 shows the release of HTB from polymer 3A in rat plasma following the method described in example 5.

The results obtained in this assay are shown in FIG. 11, wherein a time-dependent release of HTB from polymer 3A is observed.

EXAMPLE 6

Example of the Preparation of a Coating with a Polymer of Formula I

Commercial Goretex® vascular grafts were immersed into a 1:1 dioxane/ethanol solution of the polymer of example 2 (2 wt %) for 30 min. The wet segments of the prostheses were dried at room temperature in a controlled atmosphere of nitrogen until constant weight. The thickness and quantity of the coating was determined by measuring the weight gain of the coated prostheses with respect to the original uncoated prostheses. Homogeneous coatings having a thickness of about 3–5 μm were obtained.

Coated Goretex prostheses were then tested in an extracorporeal circuit and the coating was shown to be stable under blood flux conditions for five days by gravimetry and scanning electron microscopy (SEM).

Similar results were obtained using polymer 3A obtained in example 3.

EXAMPLE 7

Assessment of the Thrombogenic Properties of a Non-Biological Material Coated with a Polymer of the Invention The effect of the application of a polymer of the invention as coating of a non-biological material upon the thrombogenic properties of the latter can be evaluated in vitro by measuring the platelet aggregation on a material coated with a polymer of the invention in comparison to that observed in the uncoated material; platelet aggregation can be monitored by determining the amount of platelets retained on the material or by scanning electron microscopy (SEM).

a) Method

For this study, platelet-rich plasma (PRP) from sheep arterial blood was used. PRP was isolated by centrifugation of 40 mL blood at 1500 rpm for 10 min. After this time, the supernatant was discarded and the content of platelets was determined with a hematologic counter Serono-3000. The non-biological material used in this assay were Goretex® vascular grafts of 4 mm inner diameter. A group of prostheses coated with a polymer and a control group (uncoated prostheses) were used.

Prostheses were mounted on seeding chambers and 100 μL of PRP was added. Chambers were incubated at 37° C. in an incubator (5% CO2) during different periods of time. After the assay time, prostheses were washed three times with MEM (Minimal Essential Medium) to remove non-retained platelets and the number of platelets retained in the prostheses in comparison with the control group was determined indirectly by counting the number of platelets recovered at each of the assay times.

After this, samples were fixed with glutaraldehyde, washed with buffered solution (pH 7.4), dehydrated in a graded acetone series and metallized with gold/palladium for their examination by SEM using a scanning electron microscope Zeiss 950 DSM.

b) Results

Using this assay, it has been observed that the coating of Goretex® prostheses with a thin layer of the polymer obtained in example 2 following the method disclosed in example 6 decreases the retention of platelets in comparison with the uncoated prostheses. In addition, the analysis by SEM shows that platelets are less aggregated in the case of coated prostheses, while the uncoated prostheses (control group) present coagulated domains of aggregated platelets with a strong adhesion to the porous structure of the surface of Goretex®.

These results show the utility of the polymers of the invention to improve the thrombogenic properties of non-biological materials that are in contact with the blood during use.

What is claimed is:

1. A polymeric compound of relative general formula I

wherein:
A represents a residue of a polymerisable acrylic or vinylic monomer carrying triflusal or HTB, wherein triflusal or HTB are linked to the remainder of the monomer molecule through an in vivo hydrolysable covalent bond;
B represents a residue of a second polymerisable monomer;
m and n represent the molar fractions of the monomers A and B in the polymer so that m+n is always 1 and m is always different from 0;
and wherein the A and B units are distributed randomly in the polymer.

2. A compound according to claim 1 wherein the hydrolysable covalent bond through which triflusal or HTB are linked is a carboxylic ester bond.

3. A compound according to claim 1 wherein n represents 0.

4. A compound according to claim 1 wherein n is different from 0.

5. A compound according to claim 1 of relative formula Ia:

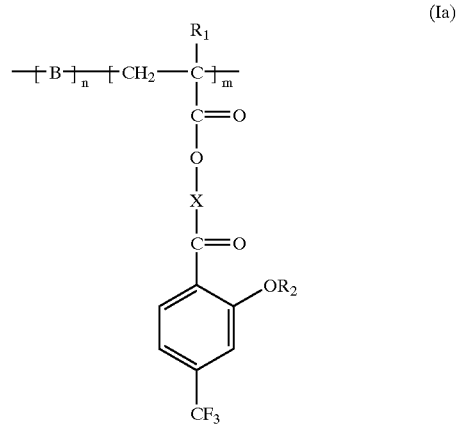

wherein:
$R_1$ represents hydrogen or $C_{1-4}$ alkyl;
$R_2$ represents —$COCH_3$ or hydrogen;
X represents —$(CH_2CH_2O)_p$—;
p represents an integer from 1 to 100; and
B, m and n have the meaning described in claim 1.

6. A compound according to claim 5 wherein $R_1$ represents methyl and p represents 1.

7. A compound according to claim 6 wherein n represents 0.

8. A compound according to claim 6 wherein n is different from 0.

9. A compound according to claim 8 wherein B represents a residue of 2-hydroxyethyl methacrylate, methyl methacrylate, methyl acrylate, N-vinylpyrrolidone, acrylic acids methacrylic acid, acrylamide, N,N-dimethylacrylamide, vinyl acetate or 2-acrylamido-2-methylpropanesulfonic acid.

10. A compound according to claim 9 wherein B represents a residue of N,N-dimethylacrylamide.

11. A compound according to claim 9 wherein B represents a residue of 2-acrylamido-2-methylpropanesulfonic acid.

12. A compound according to claim 1 having an average molecular weight between 10000 and 100000 Daltons.

13. A compound according to claim 7 wherein $R_2$ represents —$COCH_3$.

14. A compound according to claim 13 having an average molecular weight of 48000 Daltons, a polydispersity index of 1.8 and $^1H$ and $^{13}C$ NMR spectra in accordance with the ones shown in FIG. 3.

15. A compound according to claim 10 wherein $R_2$ represents —$COCH_3$.

16. A compound according to claim 11 wherein $R_2$ represents —$COCH_3$.

17. A compound according to claim 15 with a molar fraction m of about 0.2 and a molar fraction n of about 0.8, an average molecular weight of 33000 Daltons, a polydispersity index of 2.4 and $^1H$ and $^{13}C$ NMR spectra in accordance with the ones shown in FIG. 5.

18. A compound according to claim 15 with a molar fraction m of about 0.4 and a molar fraction n of about 0.6, an average molecular weight of 34000 Daltons, a polydispersity index of 2.6 and a $^1H$ NMR spectrum in accordance with that shown in FIG. 8.

19. A compound according to claim 15 with a molar fraction m of about 0.6 and a molar fraction n of about 0.4, an average molecular weight of 35000 Daltons, a polydispersity index of 2.5 and a $^1H$ NMR spectrum in accordance with that shown in FIG. 7.

20. A compound according to claim 15 with a molar fraction m of about 0.8 and a molar fraction n of about 0.2, an average molecular weight of 38000 Daltons, a polydispersity index of 2.8 and a $^1H$ NMR spectrum in accordance with that shown in FIG. 6.

21. A compound according to claim 16 with a molar fraction m of about 0.8 and a molar fraction n of about 0.2, an average molecular weight of 43000 Daltons, a polydispersity index of 2.5 and $^1H$ and $^{13}C$ NMR spectra in accordance with the ones shown in FIG. 10.

22. A process for the preparation of a polymeric compound of formula I according to claim 1 which comprises the radical polymerization of a monomer A and optionally a second monomer B in the molar fractions m and n, respectively, wherein A, B, m and n have the meaning described in claim 1, in the presence of a polymerization initiator, in a suitable solvent.

23. A device or article which comprises a surface of a non-biological material coated with a polymer carrying triflusal or HTB of formula I according to claim 1, wherein said device is suitable for insertion into the body of a mammal and following insertion, is in contact with blood.

24. A device or article according to claim 23 which is a vascular prosthesis, an artificial cardiac valve or a stent.

25. Process for preparing a device or article according to claim 23 or 24 which comprises coating said device or article with a polymer carrying triflusal or HTB of formula I according to claim 1.

26. A pharmaceutical composition which comprises a polymeric compound of formula I according to claim 1 and one or more pharmaceutically acceptable excipients.

* * * * *